United States Patent [19]

Aldridge, Jr.

[11] Plant 4,836

[45] Apr. 6, 1982

[54] *NERIUM INDICUM*—LITTLE RED VARIETY

[75] Inventor: Richard C. Aldridge, Jr., Von Ormy, Tex.

[73] Assignee: Aldridge Nursery, Inc., Von Ormy, Tex.

[21] Appl. No.: 192,093

[22] Filed: Sep. 29, 1980

[51] Int. Cl.[3] ..... A01H 5/00

[52] U.S. Cl. ..... Plt./54

[58] Field of Search ..... Plt./54

*Primary Examiner*—Robert E. Bagwill

*Attorney, Agent, or Firm*—Burns, Doane, Swecker & Mathis

[57] ABSTRACT

A new and distinct variety of *Nerium indicum* is provided which has a dwarf growth habit, small leaves, highly attractive deep scarlet red flowers, and superior hardiness. The seed parent of the new variety was of the Single Hardy Red variety and the pollen parent was of the Scarlet Beauty variety.

6 Drawing Figures

SUMMARY OF THE INVENTION

The seed parent of the new variety was of the Single Hardy Red variety (non-patented) which is sometimes identified as the Nerium Single Hardy Red, Single Hardy Red Oleander, or Nerium Cardinal. This parent was a standard variety of *Nerium indicum* which has been in cultivation for over sixty years and is widely distributed in South Texas and throughout the United States Gulf Coast region. It grows with age generally as broad as it is tall and reaches at maturity a height of 12 to 18 feet depending upon soil conditions. The flowers are single, bright medium red in color and are produced in profusion in good sized clusters during late spring. It will commonly withstand temperatures as low as 15° F. without freeze damage.

The pollen parent of the new variety was of the Scarlet Beauty variety (non-patented) which is sometimes identified as Nerium Scarlet Beauty or Scarlet Beauty Oleander. This pollen parent variety was selected by me as a chance seedling during the summer of 1948. This parent variety of *Nerium indicum* has very attractive deep scarlet flowers which are of the darkest red of any previously known Oleander. It blooms profusely during mid-spring, occasionally during the summer months, and again during the early fall, and has a distinctive habit of growth which is rather upright and approximately one-half as wide as it is tall at any age. This parent variety was commercially distributed for a number of years, but commercial sales were discontinued approximately ten years ago primarily because of its lack of cold hardiness. It commonly will freeze back to ground level at 30° F. which seriously limits its usefulness to USDA climatic Zone 10 and the southern part of Zone 9.

On May 25, 1958 blooms of the Single Hardy Red variety were hand pollinated with pollen from the Scarlet Beauty variety at Von Ormy, Texas. Accordingly, the parentage of the new variety can be expressed as follows:

SINGLE HARDY RED×SCARLET BEAUTY.

The seed which formed was harvested during late 1958 and was planted in flats in a greenhouse for germination. In early spring of 1959 two hundred seedlings were transplanted from these two flats into three inch standard clay pots. These potted seedlings were next placed in a lath-house for further growing. On Dec. 5, 1959 these seedlings were transplanted to an open field area (Lot 26, Block 68) for observation and evaluation. As a result of these studies, it was determined that nearly all of the seedlings were inferior to the original parental varieties. However, three plants appeared to be worthy of further consideration and were preserved. The remaining seedlings were destroyed during the winter of 1966.

One of the three remaining seedlings was selected primarily because of its distinctive dwarf growing characteristics and its demonstrated cold hardiness. On Apr. 19, 1967 cuttings were taken from this plant and were placed in a greenhouse propagating area where they were subsequently rooted and planted in three inch standard clay pots. These potted cuttings were placed in a lath-house for further growing. On June 13, 1968 fifty-two plants of the new variety were taken from the lath-house area and were transplanted to an open field (Lot 6, Block 72) growing environment for further study and evaluation.

It has been confirmed that the new variety of *Nerium indicum* is characterized by:

(a) a dwarf growth habit which produces an overall plant one-half or less the size of the Single Hardy Red variety in any given period and which after several years is approximately as broad as it is tall, (b) the formation of deep scarlet red flowers which are smaller than those of the single Hardy Red and Scarlet Beauty varieties and substantially identical in color to those of the Scarlet Beauty variety, (c) the formation of leaves approximately one-half the size of the leaves of the Single Hardy Red variety, and (d) superior hardiness compared to the Scarlet Beauty variety.

The characteristics of the new variety obtained as indicated above are fully transmissible by asexual propagation. The new variety has been designated the LITTLE RED variety.

BRIEF DESCRIPTION OF THE PHOTOGRAPHS

The accompanying photographs show as nearly true as it is reasonably possible to make the same in color illustrations of this character typical specimens of plants and plant parts of the new variety. For comparative purposes similar illustrations for the previously known Single Hardy Red variety also are presented. The plants illustrated were grown at Von Ormy, Tex.

DETAILED DESCRIPTION

The plants described were grown at Von Ormy, Tex.

Figure 1:
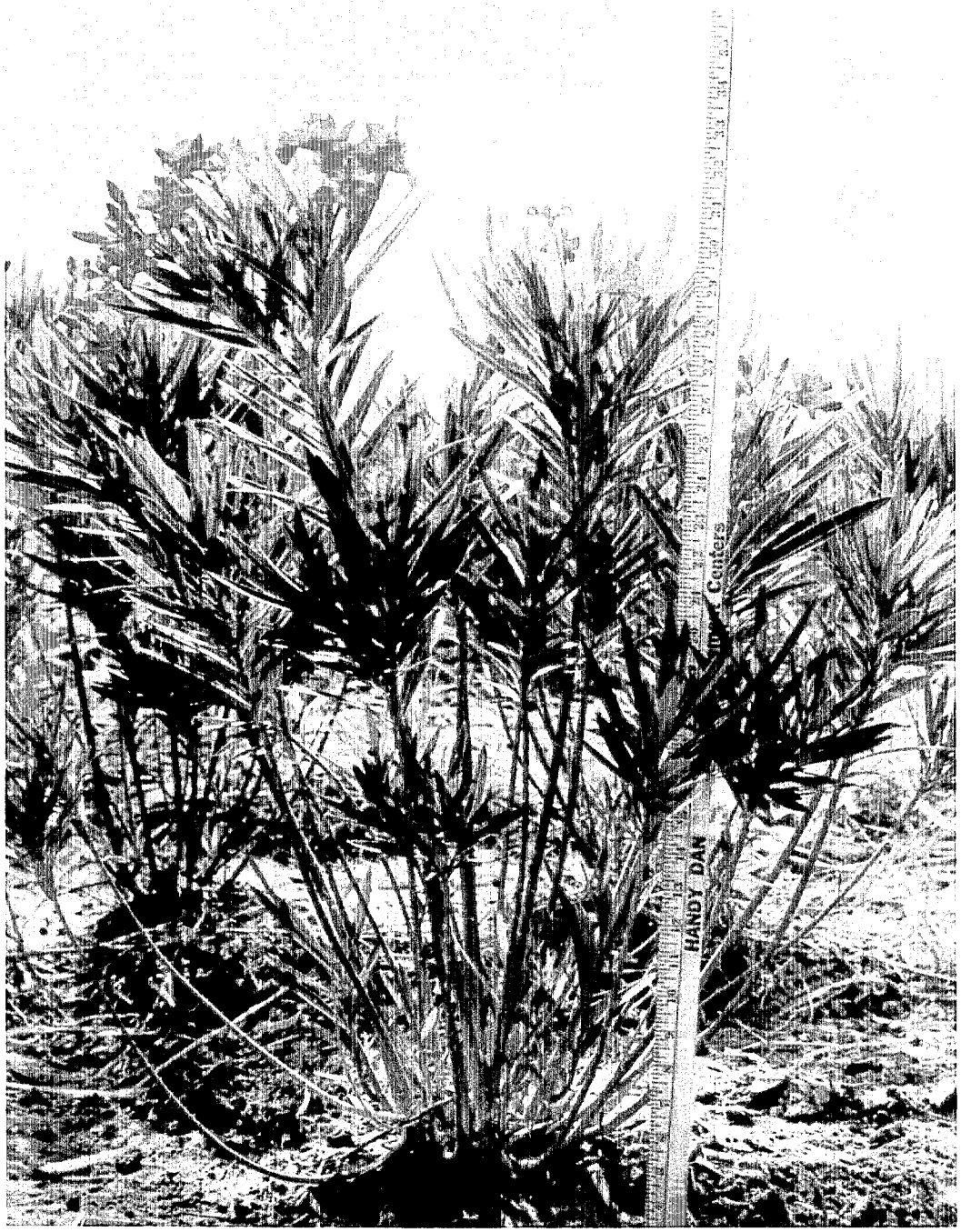
FIG. 1 shows a typical plant of the Little Red variety which is four years old and less than three feet in height and breadth.
Figure 2:
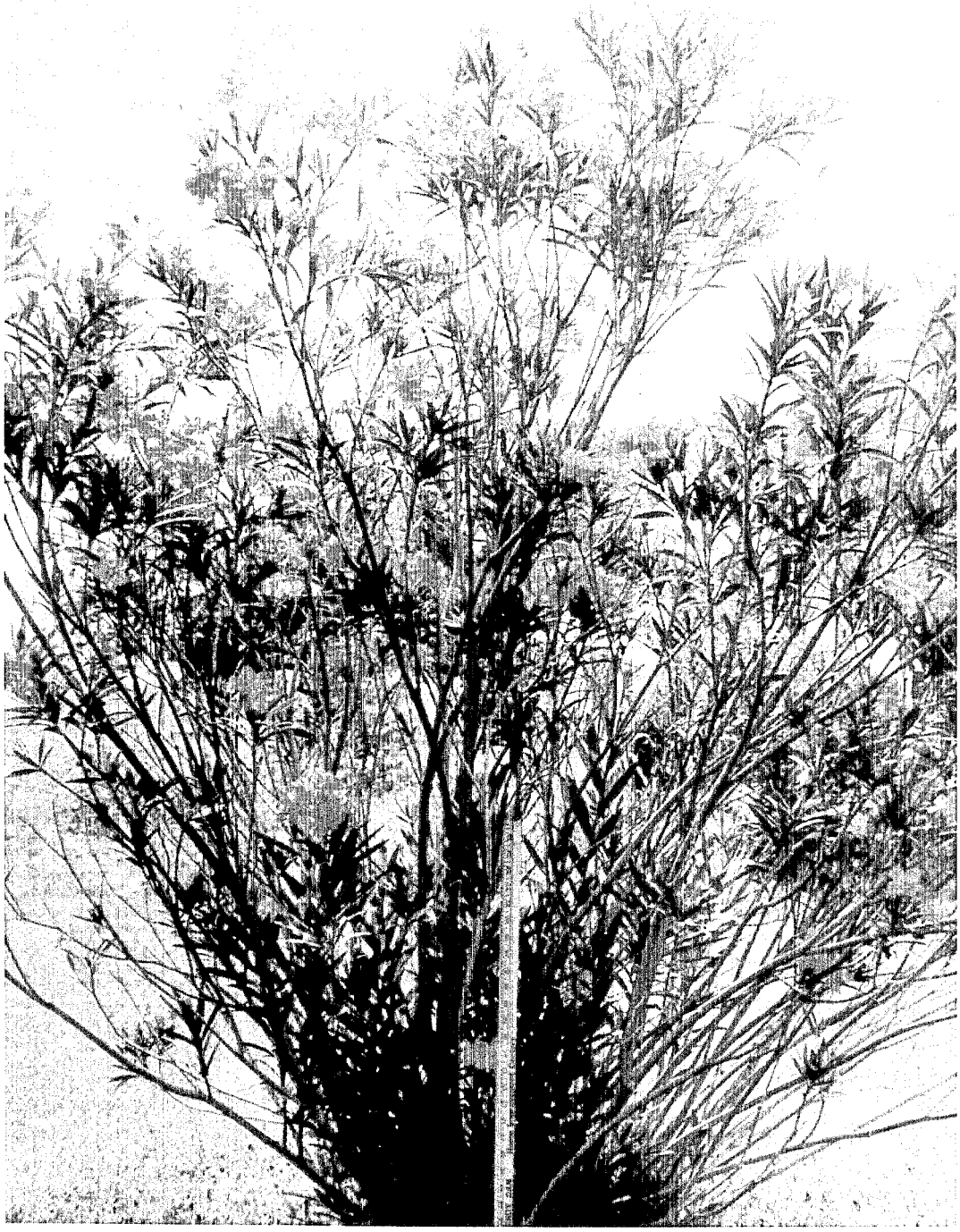
FIG. 2 shows a typical plant for comparative purposes of the Single Hardy Red variety which is six years old and over eight feet in height and breadth. At the age of twelve years plants of the Little Red variety are only approximately six feet in height and breadth.

The Little Red variety of *Nerium indicum* is an erect evergreen shrub which possesses a distinctive dwarf growth habit which makes it a valuable addition to the presently available varieties. It produces a plant approximately one-half or less the size of the standard Single Hardy Red variety at any given period. As illustrated in FIG. 1, a four year old plant of the Little Red variety is less than three feet in height and breadth. At the age of twelve years plants of the Little Red variety are only approximately six feet in height and breadth. As illustrated in FIG. 2, plants of the Single Hardy Red variety at the age of six years are already over eight feet in height and breadth.

Figure 3:
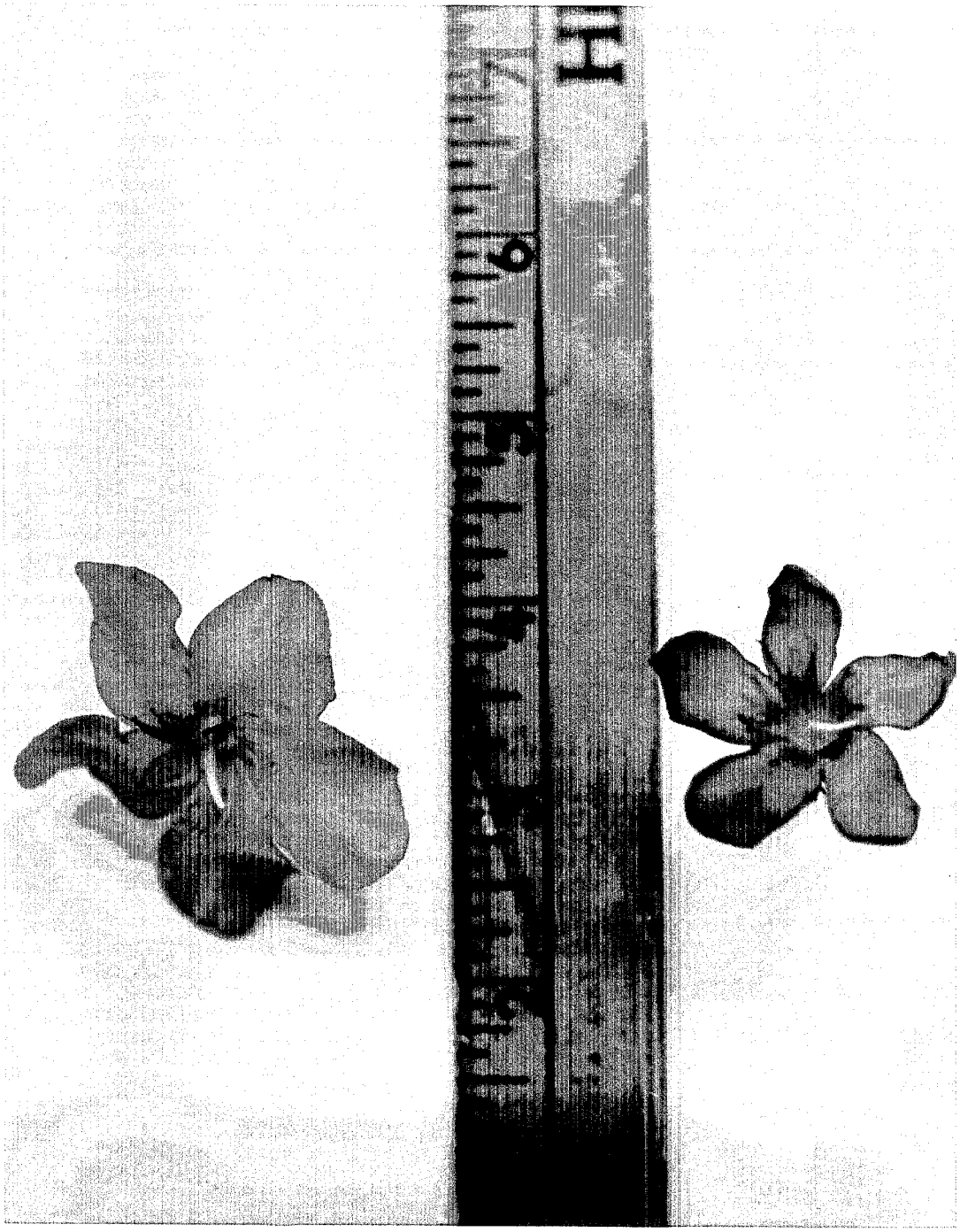
FIG. 3 shows on the right a typical deep scarlet red flower of the Little Red variety, and on the left the larger and lighter red flower of the Single Hardy Red variety. The color of the flower of the Little Red variety in this paragraph is more accurately depicted than in FIG. 1.
Figure 4:
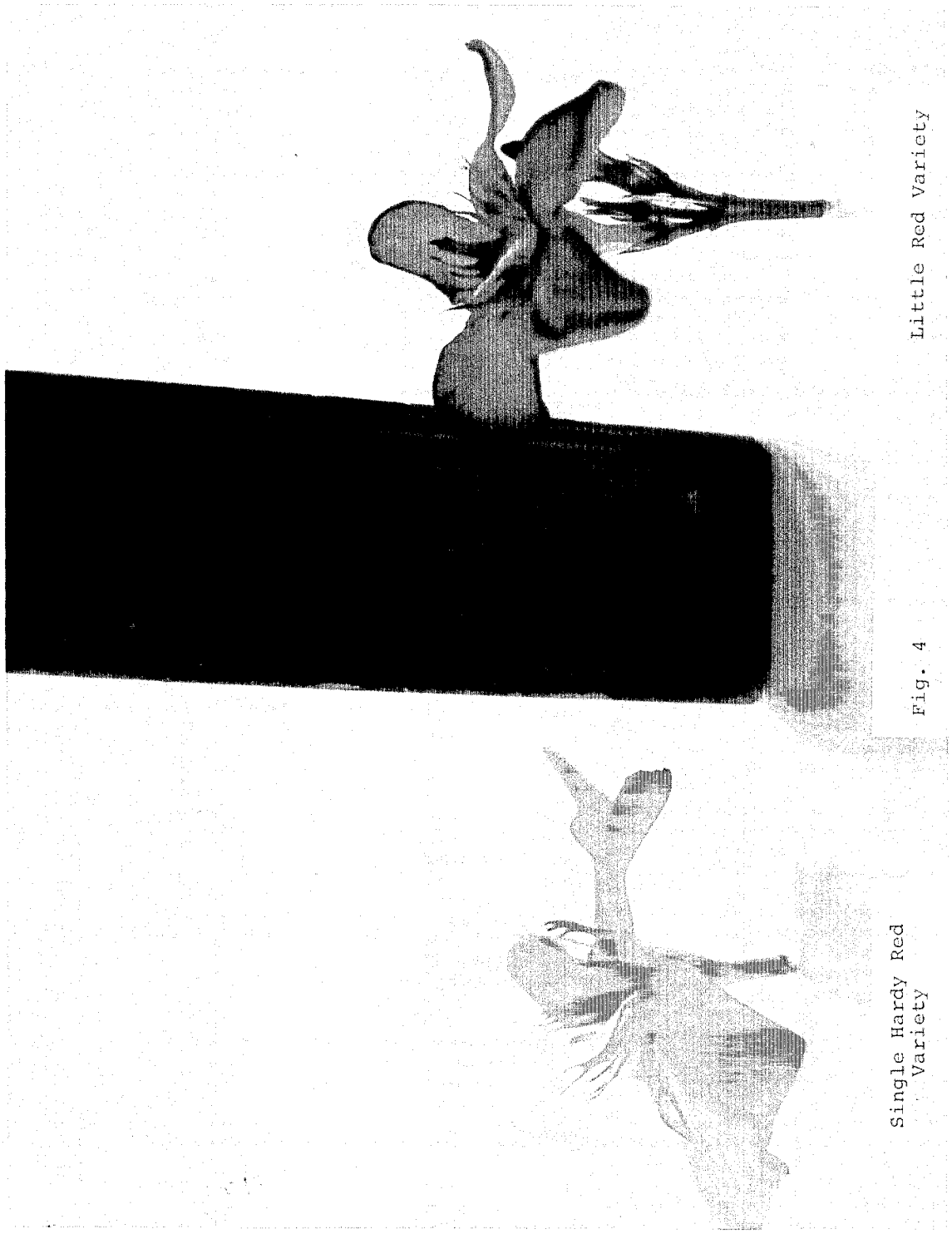
FIG. 4 shows the flowers of FIG. 3 as viewed from the side.
Figure 5:
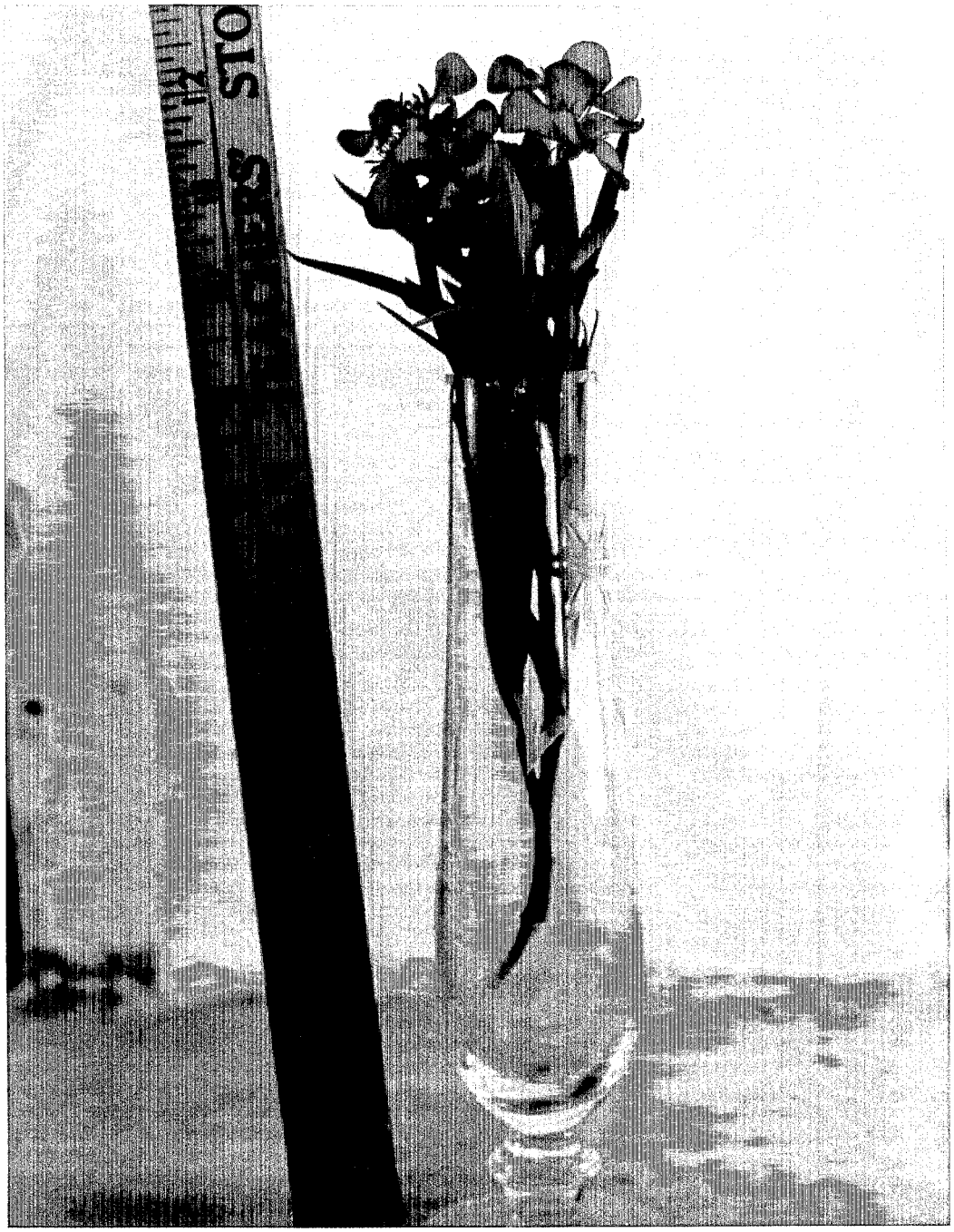
FIG. 5 shows a typical flowering branch of the Little Red variety.

The Little Red variety at Von Ormy, Tex. blooms in late spring or early summer depending upon the weather conditions. The flowers are single, five-lobed, corolla-tube funnel formed, and possess a distinctive deep scarlet red color. The outer edge of the petals is black which frames the deep scarlet coloration. The deep scarlet red flower coloration of the Little Red variety is substantially identical to that of the Scarlet Beauty variety, and approaches that of 46/A (red group) of the R.H.S. Colour Chart of the Royal Horticultural Society if one disregards the black petal edges. As illustrated in FIG. 3, the flowers of the Single Hardy Red variety are of a lighter medium red coloration which includes more of a purple cast. Additionally, the flowers of the Little Red variety are smaller than those of either of its parents, and as illustrated in FIG. 3, the flowers of the Little Red variety are only approximately seventy-five percent or less the size of the Single Hardy Red variety. The compound terminal flower clusters or cymes of the Little Red variety are also smaller than those of the Single Hardy Red variety.

Figure 6:
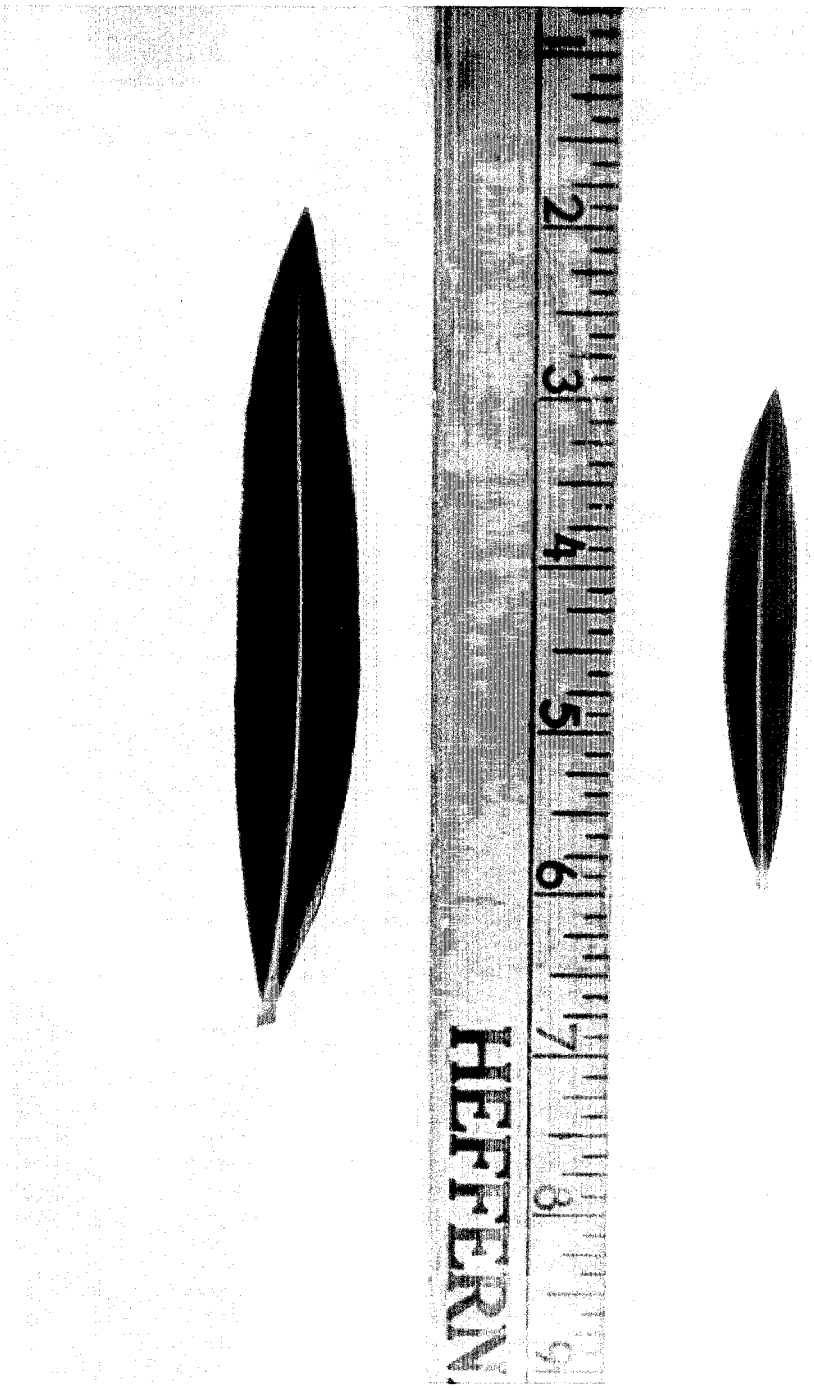
FIG. 6 shows on the right a typical leaf (upper surface) of the Little Red variety, and on left the larger leaf (upper surface) of the Single Hardy Red variety.

The leaves of the Little Red variety are substantially smaller than those of the standard Single Hardy Red variety, and as illustrated in FIG. 6, the leaves of the Little Red variety are approximately one-half the size of the leaves of the Single Hardy Red variety. The leaf appearance with the exception of size is substantially identical to that of the Single Hardy Red variety. The leaves are numerous, opposite or in whorls of 3 or 4, elliptic, smooth margined, firm to leathery, and dark green (upper surface) and glabrous with a conspicuous yellow-green main vein. The under surface is a paler green with numerous delicate almost parallel lateral veins.

An outstanding characteristic of the Little Red variety is its ability to withstand cold temperatures. For instance, the plants of the variety which were planted in open field conditions at Von Ormy, Tex. on June 13, 1968 have never been damaged by cold weather. The most significant freeze during this period occurred on Mar. 3, 1980 when the temperature dropped to 16° F. This late freeze severely damaged many broadleaf evergreens growing at the same area including *Ligustrum lucidum, Buxus japonica, Eriobotrya japonica, Pittosporum tobira,* and *Podocarpus maki.* However, not one leaf nor stem-tip of the Little Red variety showed any damage. The photograph of FIG. 1 was taken on May 31, 1980 less than ninety days after this hard freeze. It is conservatively estimated that the Little Red variety will withstand temperatures of 15° F. with no injury. No other dwarf Oleander is known to possess this attribute with such other dwarf plants being incapable of tolerating temperatures below 28° to 30° F.

I claim:

1. A new and distinct variety of *Nerium indicum* resulting from a cross of the Single Hardy Red variety and the Scarlet Beauty variety, substantially as shown and described, characterized by:

(a) a dwarf growth habit which produces an overall plant one-half or less the size of the Single Hardy Red variety in any given period and which after several years is approximately as broad as it is tall, (b) the formation of deep scarlet red flowers which are smaller than those of the Single Hardy Red and Scarlet Beauty varieties and substantially identical in color to those of the Scarlet Beauty variety, (c) the formation of leaves approximately one-half the size of the leaves of the Single Hardy Red variety, and (d) superior hardiness when compared to the Scarlet Beauty variety.

* * * * *

Little Red Variety

Single Hardy Red
Variety

Single Hardy Red Variety

Little Red Variety

Single Hardy Red Variety

Little Red Variety

Little Red Variety

Single Hardy Red Variety

Little Red Variety